| United States Patent [19] | [11] Patent Number: 4,933,500 |
|---|---|
| Chabardes et al. | [45] Date of Patent: Jun. 12, 1990 |

[54] PROCESS FOR THE PREPARATION OF CITRAL

[75] Inventors: Pierre Chabardes, Ste Foy Les Lyon; Jacques Chazal, Saint-Fons, both of France

[73] Assignee: Rhone-Poulenc Sante, Antony, France

[21] Appl. No.: 351,833

[22] Filed: May 15, 1989

[30] Foreign Application Priority Data

May 16, 1988 [FR] France .................. 88 06524

[51] Int. Cl.$^5$ .................. C07C 45/00; C07C 45/51
[52] U.S. Cl. .................. 568/460; 568/449; 568/465; 568/458; 568/485; 568/489
[58] Field of Search .............. 568/449, 450, 458, 460, 568/465, 485, 989

[56] References Cited

U.S. PATENT DOCUMENTS

| 3,943,166 | 3/1976 | Aycock | 568/460 |
|---|---|---|---|
| 4,551,560 | 11/1985 | Rizkalla | 568/465 |
| 4,562,296 | 12/1985 | Hargis | 568/465 |

FOREIGN PATENT DOCUMENTS

| 2157035 | 5/1973 | Fed. Rep. of Germany | 568/460 |
|---|---|---|---|
| 9559 | 7/1962 | Japan | 568/460 |
| 6095142 | 8/1981 | Japan | 568/460 |

*Primary Examiner*—Werren B. Lone
*Attorney, Agent, or Firm*—Stevens, Davis, Miller & Mosher

[57] ABSTRACT

Citral is prepared from prenol and prenal by condensation to form an acetal followed by cracking, both operations being effected in the presence of a lithium halide (e.g. lithium chloride) as catalyst.

8 Claims, No Drawings

PROCESS FOR THE PREPARATION OF CITRAL

The present invention relates to the preparation of citral from prenal and prenol.

According to French Pat. No. FR 74/40,959 (2,246,529) it is known to prepare citral by cracking the diprenyl acetal of prenal, which is itself obtained by condensation of two moles of prenol with one mole of prenal. The condensation of prenol with prenal is carried out in the presence of a condensing agent which is preferably an ammonium salt such as ammonium nitrate, and of a dehydrating agent which may be calcium sulphate or a molecular sieve, and the pyrolysis of the diprenyl acetal thus obtained is carried out by heating to a temperature of between 120 and 230° C., optionally in the presence of an acidic catalyst such as p-toluenesulphonic, o-nitrobenzoic acid or sodium hydrogen sulphate.

It has now been found, and this is what forms the subject matter of the present invention, that the condensation and the pyrolysis may be carried out using a lithium halide, and more particularly lithium chloride, as a catalyst.

The present invention accordingly provides a process for the preparation of citral which comprises condensing prenol with prenal in a molar ratio of at least 2:1 and in the presence of a lithium halide as catalyst to produce the diprenyl acetal of prenal, and then cracking the said acetal also in the presence of a lithium halide as catalyst.

The acetalization is carried out using at least two moles of prenol per mole of prenal and generally by operating in an inert organic solvent such as an aromatic hydrocarbon e.g. toluene, at a temperature of 70° to 100° C. so that the water formed is entrained by azeotropic distillation. It may be advantageous to operate under reduced pressure, generally between 20 and 100 mm Hg (2.7 to 13.3 kPa), depending on the nature of the solvent employed.

The cracking of the diprenyl acetal of prenal is generally carried out by heating to a temperature of between 120° and 150° C. in the presence of the lithium halide, preferably lithium chloride, the operation being carried out in a suitable organic solvent such as 1,2-dichlorobenzene. It may be advantageous to operate under reduced pressure, generally close to 100 mm Hg (13.3 kPa).

In the process of the invention, it is unnecessary to isolate the diprenyl acetal of prenal before performing the cracking. In this case, it is not necessary to add more lithium halide to perform the cracking, since the lithium halide present in the crude product of the acetalization stage is used.

It may be particularly advantageous to operate the acetalization and cracking steps in the presence of a polymerization inhibitor such as hydroquinone.

In the process of the invention, from 0.01 to 0.1 mole of lithium halide is generally employed per mole of prenal or of the diprenyl acetal of prenal.

The process of the invention makes it possible to obtain citral selectively in yields which are generally higher than 60% relative to the prenal converted, the degree of conversion of prenal being generally higher than 75%.

The following Example illustrates the invention.

EXAMPLE

Prenal of 97.2% purity (35.1 g, 405.58 mmol), pure prenol (87 g, 1010.22 mmol), toluene (11.5 cc) and hydroquinone (0.1 g) are introduced into a round-bottom flask fitted with a distillation column. Lithium chloride (0.34 g, 8.02 mmol) is added and the mixture is then heated for 2 hours 30 minutes under reduced pressure (80 mm Hg; 10.7 kPa) to a temperature of between 75° and 79° C. while the water formed (3 cc) is entrained azeotropically. Lithium chloride (0.34 g) is added again and heating is continued for 2 hours under reduced pressure (80 mm Hg; 10.7 kPa) at a temperature of between 82° and 86° C. while the water formed (5.2 cc in all) is entrained azeotropically. After removal of the toluene by distillation, the round-bottom flask contains a pale yellow oil (117.68 g) containing the diprenyl acetal of prenal.

Analysis of the reaction mixture shows that the degree of conversion of prenal is 73% and that the yield of the diprenyl acetal of prenal is 93% based on the prenal converted.

To the crude diprenyl acetal of prenal (116.8 g) obtained previously, which analysed 55.8% by titration, i.e. 271.74 mmol, 1,2-dichlorobenzene (10 g) is added. After the excess prenol and unreacted prenal have been removed by distillation under reduced pressure (15 mm Hg; 2 kPa), the mixture is heated under reduced pressure (90 mm of mercury; 12 kPa) for 3 hours 30 minutes at a temperature of between 135° and 142° C. A distillate (80 cc, 70.9 g) is collected. The residue (54.2 g) in the flask is an orange-yellow oil consisting essentially of citral.

Analysis of the reaction mixture shows that the degree of conversion of the diprenyl acetal of prenal is 70% and that the yield of citral is 96%, based on the acetal converted.

We claim:

1. A process for the preparation of citral which comprises condensing prenol with prenal in a molar ratio of at least 2:1 and in the presence of a lithium halide as catalyst to produce the diprenyl acetal of prenal, and then
   cracking the said acetal also in the presence of a lithium halide as catalyst.
2. Process according to claim 1, wherein the lithium halide catalyst used is lithium chloride.
3. Process according to claim 1, wherein 0.01 to 0.1 mole of lithium halide catalyst is employed per mole of prenal used.
4. Process according to claim 1, wherein the condensation is carried out at a temperature of 70° to 100° C. in an inert organic solvent and the water formed is removed by azeotropic distillation.
5. Process according to claim 4 wherein the condensation is carried out under reduced pressure.
6. Process according to claim 1, wherein the cracking is carried out at a temperature of 120° to 150° C.
7. Process according to claim 6 wherein the cracking is carried out under reduced pressure.
8. Process according to claim 1, wherein the lithium halide present in the product of the condensation is used as the catalyst in the cracking.